United States Patent [19]

Klausz

[11] Patent Number: 4,633,494
[45] Date of Patent: Dec. 30, 1986

[54] METHOD OF CONTROLLING THE POSITIONING OF A PATIENT WITH RESPECT TO AN X-RAY DEVICE AND INSTALLATION FOR CARRYING OUT SUCH METHOD

[75] Inventor: Remy Klausz, Neuilly sur Seine, France

[73] Assignee: Thomson-CGR, Paris, France

[21] Appl. No.: 704,851

[22] Filed: Feb. 25, 1985

[30] Foreign Application Priority Data

Feb. 28, 1984 [FR] France .................. 84 03040

[51] Int. Cl.⁴ .................................. A61B 6/08
[52] U.S. Cl. ........................... 378/205; 378/91; 378/99; 358/111; 358/93
[58] Field of Search ............ 378/20, 205, 91, 99, 378/209; 358/111, 103, 107, 93

[56] References Cited

U.S. PATENT DOCUMENTS 3,777,124 12/1973 Pavkovich .................. 378/91
4,400,727 8/1983 Aron .................... 358/103

FOREIGN PATENT DOCUMENTS 0064623 of 0000 European Pat. Off. .
3213363 of 0000 Fed. Rep. of Germany .
2514329 of 0000 Fed. Rep. of Germany .
2655661 6/1978 Fed. Rep. of Germany .......... 378/4
2345983 of 0000 France .
2482444 of 0000 France .

Primary Examiner—Carolyn E. Fields
Assistant Examiner—John C. Freeman
Attorney, Agent, or Firm—Oblon, Fisher, Spivak, McClelland & Maier

[57] ABSTRACT

A method and apparatus for positioning a patient with respect to an X-ray installation. An X-ray image is produced at the beginning of the operation and stored in an image memory. The memory is read in order to visualize the X-ray image on a television receiver. The table is displaced to a desired position, and the image in the receiver is decentered so as to reproduce the image that would be observed if an X-ray were taken at the desired position.

11 Claims, 3 Drawing Figures

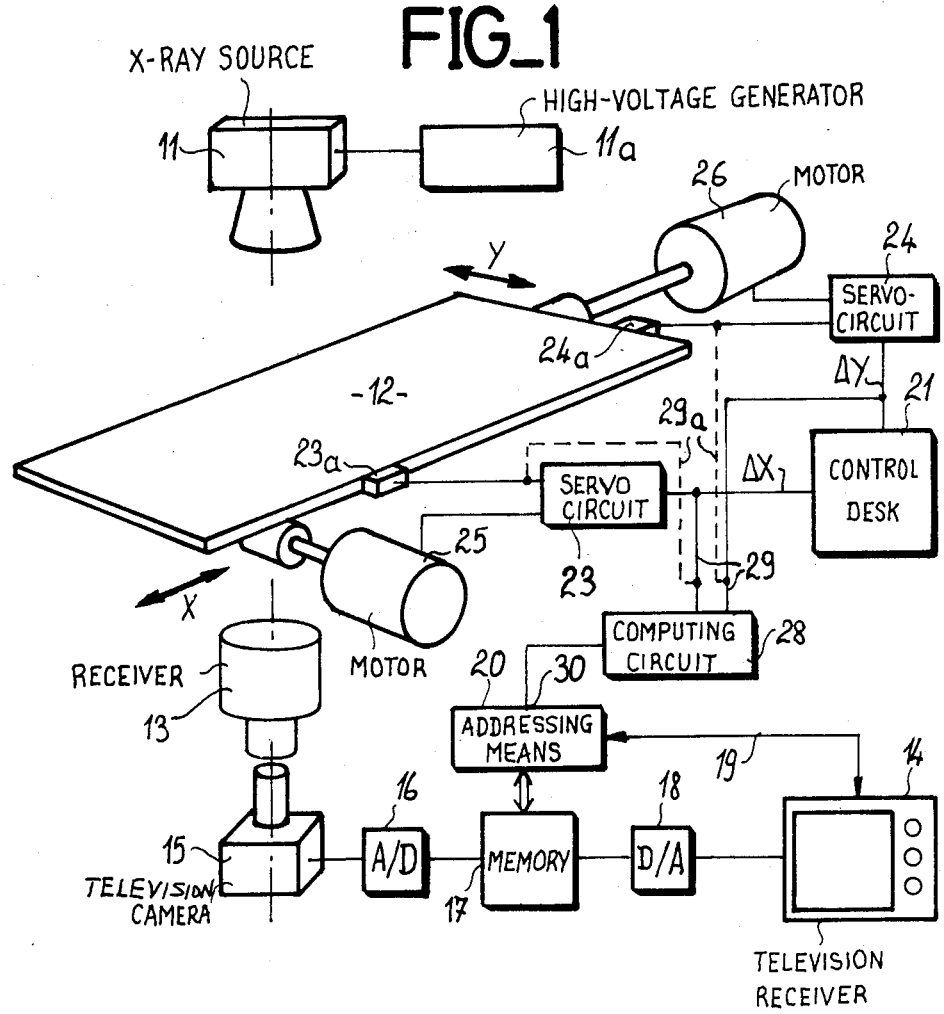
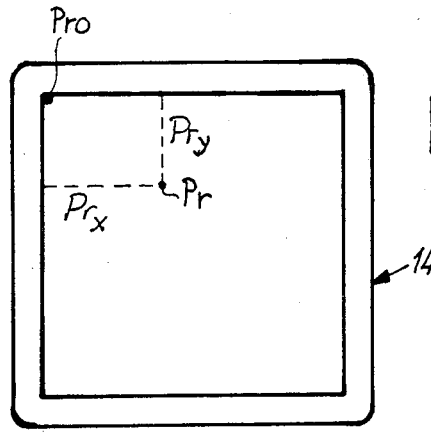

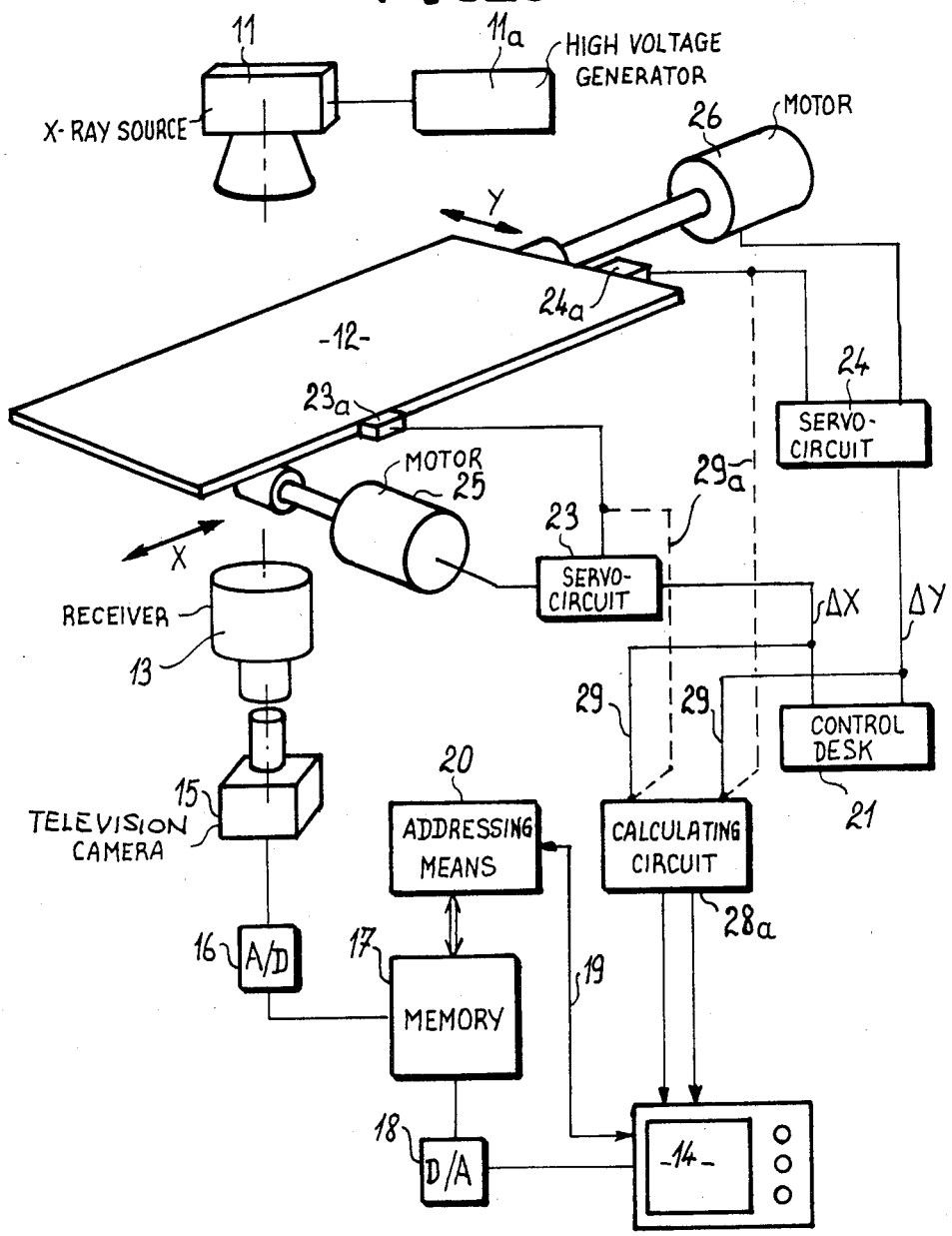

METHOD OF CONTROLLING THE POSITIONING OF A PATIENT WITH RESPECT TO AN X-RAY DEVICE AND INSTALLATION FOR CARRYING OUT SUCH METHOD

The present invention is related to a method of controlling the positioning of a patient with respect to a radiology or X-ray installation or device, wherein the radiology or X-ray image forming means are used, and allowing accurate positioning while exposing the patient only to a particularly reduced radiation. The invention is also related to an X-ray installation and device comprising means for carring out the above method.

In an X-ray room the positioning of a patient with respect to the X-ray beam is a delicate and important operation. It is obviously desirable to define the selected observation zone in a satisfactory manner, so that, on the one hand, the area to be examined occupies the major portion of the visualization means used (film, television screen or the like) and, on the other hand, so that the irradiated surface does not extend past the required zone or area. With a view to positioning the patient, one current technique has consisted in utilizing external anatomic reference points of the patient and in positioning a light beam between such reference points, said light beam simulating the X-ray beam. Such method requires the provision, in the installation, of a light source adapted to emit a light beam having the same geometrical characteristics as those of the X-ray beam. However, in practice, this method is not very accurate. Furthermore it requires the presence of an operator who has sufficient anatomic knowledge so as to be able to position correctly the light beam with respect to the external anatomic reference points. Also the latter are more or less difficult to be taken into account, depending on the patient's morphological characteristics. The only advantage of this method resides in the fact that the patient is not exposed to X-ray irradiation during the entire time period required for the positioning operation.

In the installations equipped for radioscopic examination, one might be tempted to carry out the positioning operation by applying this operation mode. However, this brings about supplementary irradiation of the patient, which is not useful to the establishment of the diagnosis properly speaking, and which is effective during the entire time period required for displacing the table supporting the patient. Now it should be noted that these displacements involve rather large masses and thus are effected comparatively slowly.

The present invention allows to obtain entirely the precision offered by the positioning by means of radioscopic observation, while yet substantially reducing the supplementary X-ray dose which is not useful to the diagnosis.

With this aspect in view, one essential object of the invention is to provide a method of controlling the positioning of a patient with respect to an X-ray installation comprising a table supporting the patient, a unit including an X-ray source and a receiver, means for controlling the relative displacements of said unit and said table, as well as a visualization system including an image memory receiving digital information data which represent an X-ray image, and means for displaying said image, said method comprising the steps of obtaining an image by briefly actuating said visualization system, reproducing said image within a given frame or perimeter of said displaying system, and inducing a relative uncentering of said image and said frame or perimeter, which represents said relative displacements.

It should be noted that the most expensive sub-assemblies listed herein-above, adapted to allow the novel method to be carried out (more particularly the image memory) exist in many modern X-ray installations. The displaying means are preferably constituted by a television receiver. The above-mentioned frame or perimeter of said displaying means represents, for example, the borders of the screen in the case where the image is uncentered with respect to said screen. However, another variant can be envisaged wherein an electrically generated mask on the screen covers the image which remains stationary on the displaying means. For this reason the invention envisages any methods and means for inducing relative decentering between the aforementioned image and the frame or perimeter.

The invention is also related to an X-ray installation of the type comprising a table for supporting a patient, a unit including an X-ray source and a receiver, means for controlling the relative displacements of said unit and said table, as well as a visualization system including an image memory which receives digital data information representing an X-ray image and means for displaying said image, said installation further comprising means for producing signals representing said relative displacements and means for relatively decentering said image with respect to said displaying means, said decentering means being piloted by said signal producing means.

When the installation comprises a movable patient supporting table said signal producing means are associated to said table so that said signals represent the displacements thereof. The invention also envisages the case where the unit comprising said X-ray source and said receiver is movable with respect to the table in at least one predetermined direction. In this case at least part of said signal producing means is associated to said unit.

The invention will be more clearly understood from the following detailed description of several embodiments of an X-ray installation carrying out the principle of the invention, said description being given with reference to the appended Figures, and by way of example, but not of limitation.

BRIEF DESCRIPTION OF THE DRAWING

FIG. 1 is a block diagram of an X-ray installation incorporating the improvements defined by the present invention;

FIG. 2 shows the displaying means of this installation and the determination of the uncentering;

FIG. 3 is a block diagram showing another X-ray installation incorporating the improvements according to the invention.

FIG. 1 shows a modern, though largely conventional X-ray installation, comprising an X-ray source 11 fed by a high-voltage generator 11a, a patient supporting table 12 movable with respect to source 11, a receiver which is constituted, in this embodiment, by a luminance amplifier 13 aligned with the axis of the beam of source 11 and a television receiver 14. In the embodiment, shown table 12 is displaceable in two directions X, Y and, in in accordance with a conventional arrangement these two directions are perpendicular to each other and respectively parallel to the length and the width of the table plate. The principle of the invention may be adapted, however, to any other type of table displacement.

A television camera 15 is coupled to the luminance amplifier 13 for sensing the X-ray image produced therein. The signals delivered by the camera are transmitted to an analog-digital converter 16 the outlet terminal of which feeds a digital image memory 17. The outlet terminal of the memory is coupled to the television receiver 14 through a digital-analog converter 18. Memory 17 has a capacity sufficiently large for storing in digital form the values of all the pixels of an image reproduced on the screen of television receiver 14. Said memory is read-out permanently by cycles under the control of addressing means 20 which are synchronized with television receiver 14 (connection 19). Memory 17 and its addressing means 20 are conventional sub-assemblies available on the professional market and thus will not be described here in a more detailed manner. As regards the present example, it may be specified that an equipment developed by the VICOM Corporation is used, wherein the operating mode of the addressing means allow in a simple and inexpensive manner the principle of the invention to be carried out in practice, as will become apparent herein-after. In a manner known per se the installation further comprises a control desk 21 adapted to receive the orders related to the displacements of table 12 in the two directions X and Y. Said control desk converts the displacement orders given by the operator into two electrical values $\Delta X$ and $\Delta Y$ which act as order voltages for servo-circuits 23, 24 piloting respectively motors 25 and 26 controlling the displacements of table 12 according to directions X and Y. Furthermore, each servo-circuit is connected to a position sensor 23a or 24a respectively coupled to the table for delivering a signal which represents the corresponding displacement of said table. All these servo-control means for motors 25 and 26 are known per se and are most frequently used outside of the field of the present invention. However, in accordance with FIG. 1, it can be considered that control desk 21 is also part of the means specifically used in accordance with the invention, since its two outlet terminals supplying the order signals $\Delta X$ and $\Delta Y$ are also connected to a computing circuit 28 (connection 29) the output of which pilots the addressing means 20. In this example calculating or computing circuit 28 and addressing means 20 constitute decentering means for decentering the image reproduced on the screen of television receiver 14. As mentioned already herein-above the arrangement of addressing means 20 is particularly well adapted to coupling to computing circuit 28 and substantially simplifies the design of the latter. Indeed, addressing means 20 are designed to read automatically the storing units of memory 17 in an order corresponding to a line-after-line and pixel-after-pixel scanning on the screen of television receiver 14, while at the beginning of each frame only the address of one reference pixel is known. Although the reference pixel may be any pixel, it will be supposed, for the sake of easier understanding, that the reading of the memory starts from this pixel for the reproduction of a given image, while the memory is scanned, or explored, by automatic incrementation of the addressing means. Consequently, when a perfectly centered image is to be obtained on the screen, it is only necessary to apply to the piloting input terminal 30 of the addressing means a digital code representing the address of the first pixel of the first line: $Pr_0$.

When considering, on the contrary, the reference system of the screen of the cathode ray tube (cf. FIG. 2) the two displacements $Pr_X$ and $Pr_Y$ allow to determine, based on $Pr_0$, a new reference pixel Pr taking into account a decentering with respect to the original image in accordance with the displacements of the table. Considering the preceding remarks, it is thus sufficient to apply to input terminal 30 the address of pixel Pr of the original image (the corresponding coordinates in the screen reference system being $Pr_X$ and $Pr_Y$) for obtaining the required decentering. This is achieved by computing circuit 28 on the basis of the signals taken up at the output terminal of control desk 21. The design of circuit 28 can be carried out by any person skilled in the art. Said circuit will include, for example, analog-logic converters if signals $\Delta X$ and $\Delta Y$ representing the displacements are voltage levels, as well as as two digital dividers which are pre-adjusted in accordance with the geometric characteristics of the system, so as to make a whole number of lines and columns of the screen correspond to displacements $\Delta X$ and $\Delta Y$, respectively. The computing circuit also comprises address generating means for converting into address code the information delivered by the dividers, and for applying said code to input terminal 30 of addressing means 20.

According a variant also shown in FIG. 1 the signals representing the displacements $\Delta X$ and $\Delta Y$, instead of being picked up by the order means (i.e. at the output terminal of desk 21), can be picked up by position detectors 23a, 24a. In this case the output terminals of said detectors are connected (connections 29a in dashed line) to the input terminals of computing circuit 28, whereas connections 29 to the desk 21 are then omitted.

The method according to the invention is carried out by means of the equipment described herein-above in the following manner. When the patient has been laid down on table 12 the operator causes a radioscopic image to be produced by briefly actuating the visualization system, i.e., more particularly, by causing X-ray source 11 to emit a brief pulse. The corresponding image is immediately stored in memory 17 and becomes apparent on the screen of television receiver 14 in a perfectly centered state at the beginning, since memory 17 is read cyclically and continuously, pixel $Pr_O$ of the recorded image being taken as reference pixel, as long as the operator has not touched the table displacement controls. When the operator acts on desk 21 for displacing the patient with respect to the unit constituted by source 11 and detector 13 the corresponding signals $\Delta X$ and $\Delta Y$ are processed in computing circuit 28 with a view to elaborating the address of a new reference pixel which appears at input terminal 30. Each time the image is renewed the corresponding decentering is increased in accordance with the displacements of table 12. When the decentering becomes too important the visualization system is again actuated during a short lapse of time, with a view to record again in memory 17 the digital information corresponding to a new, non-decentered image, and the displacement of the table is pursued while another relative decentering is initiated as explained hereinbefore. These new "pictures" taken from time to time are advantageous in that they allow new details to appear on the screen and which were not visible in the original image. They can be produced by manual control effected by the operator, or by automatic control. It may be envisaged, for example, to renew the image automatically when the surface of the decentered image on the screen decreases beyond a selected percentage of the total screen area.

FIG. 3 illustrates another and more simple variant, wherein the decentering means act directly on television receiver 14. The subassemblies which are identical to the corresponding ones shown in FIG. 1 are designated by the same reference numerals and will not be described once more. Calculating or computing circuit 28a includes no analog-digital converter; it may simply be constituted by two amplifiers having a predetermined gain, the output terminals of which are connected to the deflection means of the picture tube of television receiver 14.

Many other variants may be envisaged for carrying out the abovedefined method. Thus signals ΔX and ΔY may be converted into proportional delays which are then used for the cyclic reading of memory 17. The delay corresponding to value ΔY would then be applied, for example, at the beginning of each image reading step, whereas the delay corresponding to value ΔX would be applied at the beginning of each line reading step. Thus it will be understood that the invention covers all technical equivalents of the means used, as long as the latter are within the scope of the appended claims.

At any rate the invention is not limited to the embodiments shown and described herein; many modifications and variants may be envisaged by those skilled in the art without departing from the spirit and scope of the invention as defined in the claims appended hereto.

I claim:

1. A method of controlling the positioning of a patient with respect to an X-ray installation comprising a patient supporting table, an X-ray source an X-ray receiver, means for controlling the relative displacements of said X-ray source and said table, sensor means for measuring the said relative displacements, a visualization system including an image memory for receiving digital information representing an X-ray image, and means for displaying said image, said method comprising the steps of acquiring an image by briefly actuating said visualization system, stiring said image, reproducing said image within a determined frame of said displaying means, relatively moving said x-ray source and said table to a desired longitudinal (x) and lateral (y) position, and inducing relative decentering of said frame and said image, in order to reproduce the image that would be observed if an xray were taken at the said desired position.

2. A method according to claim 1, wherein said memory is read cyclically so as to elaborate the signals applied to a television receiver in which said image is displayed, said method further comprising the step of actuating an addressing means, for addressing said memory in accordance with said relative displacements.

3. A method according to claim 2, wherein decentering signals representing said relative displacements are produced, and wherein said signals are converted into digital data for controlling said addressing means.

4. A method according to claim 1, wherein said memory is read cyclically so as to produce the signals applied to a television receiver in which said image is displayed, and wherein decentering signals representing said relative displacements are produced and applied to deflection means of said television receiver.

5. A method according to any one of the preceding claims, further comprising the step of acquiring another x-ray image by briefly actuating said visualization system each time exact positioning is required, recording again the digital data corresponding to the thus produced non-decentered new image in said image memory, and pursuing said relative displacements while initiating a new relative decentering.

6. An X-ray installation comprising a patient supporting table, an X-ray source and an X-ray receiver, means for controlling relative displacements of said X-ray source and said table in the longitudinal (x) and lateral (y) directions, a visualization system including an image memory for receiving digital information representing an X-ray image, and means for displaying said image, said installation further comprising means for producing signals representing said relative displacements, and means for decentering said image relative to said displaying means, which are piloted by said signal producing means.

7. An installation according to claim 6, wherein said memory is of the cyclic reading type including autonomous addressing means for controlling the reading of each image and comprising a piloting input terminal adapted to receive the address of a reference pixel of said image for initiating said reading, wherein said table is movable, said means for producing signals representing said relative displacements comprise a part in common with means for piloting the displacements of said table, and computing means of a reference address of said memory, which address corresponds to said reference pixel, said calculating means receiving data in the form of signals which are picked up in said piloting means and which represent said relative displacements.

8. An installation according to claim 6, wherein said displaying means are constituted by a television receiver and wherein said means for producing signals representing said relative displacements are connected to the deflection means of said television receiver.

9. An installation according to claim 7 wherein said signals representing said relative displacements are picked up from order means of servo-means controlling motors that control said displacements of said table.

10. An installation according to claim 8, wherein said signals representating said relative displacement are picked up from order means of servo-means controlling motors that control said displacements of said table.

11. An installation according to claim 7 or 8, wherein said signals representing said relative displacements are picked up from position detectors which detect displacements in the direction of movements caused by said motors.

* * * * *